US00PP25540P2

(12) United States Plant Patent
Eveleens

(10) Patent No.: US PP25,540 P2
(45) Date of Patent: May 12, 2015

(54) CARNATION PLANT NAMED 'HILORBLI'

(50) Latin Name: *Dianthus caryophyllus*
Varietal Denomination: Hilorbli

(71) Applicant: Peter Eveleens, Aalsmeer (NL)

(72) Inventor: Peter Eveleens, Aalsmeer (NL)

(73) Assignee: Hilverda Kooij B.V., De Kwakel (NL)

( * ) Notice: Subject to any disclaimer, the term of this patent is extended or adjusted under 35 U.S.C. 154(b) by 154 days.

(21) Appl. No.: 13/986,787

(22) Filed: Jun. 4, 2013

(51) Int. Cl.
*A01H 5/00* (2006.01)

(52) U.S. Cl.
USPC ..... Plt./278

(58) Field of Classification Search
USPC ..... Plt./278, 273
See application file for complete search history.

*Primary Examiner* — Annette Para
(74) *Attorney, Agent, or Firm* — C. A. Whealy

(57) ABSTRACT

A new and distinct cultivar of Carnation plant named 'Hilorbli', characterized by its upright, somewhat outwardly spreading and uniformly mounded plant habit; freely branching habit; freely flowering habit; large orange-colored double flowers that are positioned above and beyond the foliar plane on strong peduncles; and good garden performance.

1 Drawing Sheet

Botanical designation: *Dianthus caryophyllus.*
Cultivar denomination: 'HILORBLI'.

BACKGROUND OF THE INVENTION

The present invention relates to a new and distinct cultivar of Carnation plant, botanically known as *Dianthus caryophyllus*, grown commercially as a potted and garden plant and hereinafter referred to by the name 'Hilorbli'.

The new Carnation plant is a product of a planned breeding program conducted by the Inventor in De Kwakel, The Netherlands. The objective of the breeding program is to create new potted Carnation plants that have uniform plant habit and numerous large and attractive flowers.

The new Carnation plant is a naturally-occurring whole plant mutation of *Dianthus caryophyllus* 'Bling Bling', not patented. The new Carnation plant was discovered and selected by the Inventor as a single flowering plant from within a population of plants of 'Bling Bling' in a controlled greenhouse environment in De Kwakel, The Netherlands in May, 2009.

Asexual reproduction of the new Carnation plant by terminal cuttings propagated in a controlled greenhouse environment in De Kwakel, The Netherlands since June, 2009 has shown that the unique features of this new Carnation plant are stable and reproduced true to type in successive generations of asexual reproduction.

SUMMARY OF THE INVENTION

Plants of the new Carnation have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilorbli'. These characteristics in combination distinguish 'Hilorbli' as a new and distinct Carnation plant:

1. Upright, somewhat outwardly spreading and uniformly mounded plant habit.
2. Freely branching habit.

3. Freely flowering habit.
4. Large orange-colored double flowers that are positioned above and beyond the foliar plane on strong peduncles.
5. Good garden performance.

Plants of the new Carnation differ from plants of the parent, 'Bling Bling', primarily in flower color as flowers of plants of 'Bling Bling' have yellow-colored petals with orange-colored margins.

Plants of the new Carnation can be compared to plants of *Dianthus caryophyllus* 'Sunflor Campari', disclosed in U.S. Plant Pat. No. 12,740. In side-by-side comparisons conducted in De Kwakel, The Netherlands, plants of the new Carnation differed from plants of 'Sunflor Campari' in the following characteristics:

1. Flowers of plants of the new Carnation were larger and had more petals and petaloids than flowers of plants of 'Sunflor Campari'.
2. Plants of the new Carnation and 'Sunflor Campari' differed in flower color as plants of 'Sunflor Campari' had darker orange-colored flowers.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilorbli' grown in a container.

DETAILED BOTANICAL DESCRIPTION

Plants used in the aforementioned photograph and following observations and measurements describe plants grown during the late winter and early spring in 10.5-cm containers in a glass-covered greenhouse in Aalsmeer, The Netherlands and under cultural practices which approximate those generally used in commercial potted Carnation production. During the production of the plants, day and night temperatures averaged 12° C. and light levels averaged 7,000 lux. Plants were pinched one time five weeks after planting. Plants used for the description were 20 weeks old and plants used for the photograph were 25 weeks old. In the following description, color references are made to The Royal Horticultural Society Colour Chart, 2007 Edition, except where general terms of ordinary dictionary significance are used.

Botanical classification: *Dianthus caryophyllus* 'Hilorbli'.

Parentage: Naturally-occurring whole plant mutation of *Dianthus caryophyllus* 'Bling Bling', not patented.

Propagation:

*Type*.—By terminal cuttings.

*Time to initiate roots, summer*.—About six days at 20° C. to 25° C.

*Time to initiate roots, winter*.—About eight days at 18° C.

*Time to produce a rooted young plant, summer*.—About three weeks at 20° C. to 25° C.

*Time to produce a rooted young plant, winter*.—About five weeks at 18° C.

*Root description*.—Medium in thickness, fibrous; white in color.

*Rooting habit*.—Moderate branching; medium density.

Plant description:

*Plant type and form*.—Herbaceous perennial; upright, somewhat outwardly spreading and uniformly mounded plant habit; broad inverted triangle.

*Branching habit*.—Freely-branching growth habit; when pinched, about five primary branches develop, each with about four secondary branches; dense and bushy growth habit.

*Plant height*.—About 15.1 cm.

*Plant diameter or spread*.—About 19.7 cm.

*Lateral branches*.—Length: About 8.7 cm. Diameter: About 3 mm. Internode length: About 2.5 cm. Strength: Strong. Texture: Smooth, glabrous; waxy. Color: Close to 136B; waxy cuticle, close to 188A.

*Leaf description*.—Arrangement: Opposite, simple; sessile. Length: About 6.2 cm. Width: About 4.5 mm. Shape: Narrowly oblanceolate. Apex: Acute. Base: Attenuate, decurrent. Margin: Entire. Texture, upper and lower surfaces: Smooth, glabrous; waxy. Venation pattern: Parallel. Color: Developing leaves, upper and lower surfaces: Close to 137A to 137B; towards the base, close to 145A. Fully expanded leaves, upper surface: Close to N137A to N137D; waxy cuticle, close to 189A; venation, close to N137A to N137D and 189A. Fully expanded leaves, lower surface: Close to N137A to N137D; waxy cuticle, close to 189A; venation, close to 143A.

Flower description:

*Flower type and habit*.—Rotate double flowers usually arranged in terminal sprays; freely flowering habit with typically about 60 flowers developing per plant; flowers positioned above and beyond the foliar plane on strong peduncles; flowers face mostly upright to outwardly.

*Fragrance*.—Moderately fragrant; clove-like, sweet.

*Natural flowering season*.—Flowering is continuous through the summer and late summer in The Netherlands; plants begin flowering about twelve weeks after planting.

*Flower longevity*.—Flowers last about ten days on the plant; flowers not persistent.

*Spray height*.—About 4.1 cm.

*Spray diameter*.—About 5.6 cm.

*Flower diameter*.—About 5.4 cm.

*Flower depth*.—About 4.1 cm.

*Flower buds*.—Length: About 1.8 cm. Diameter: About 1.3 cm. Shape: Ovate. Color: Close to 137B; base, close to 144B and 145A; upper half covered with waxy cuticle, close to 188A.

*Petals and petaloids*.—Quantity and arrangement: About 52 petals and petaloids per flower arranged in numerous whorls. Length: About 3.8 cm. Width: About 2.2 cm. Shape: Spatulate. Apex: Praemorse. Base: Acute. Margin: Entire. Texture, upper and lower surfaces: Smooth, glabrous; velvety. Color: When opening, upper surface: Close to 39A; towards the base, close to 145C to 145D. When opening, lower surface: Close to 39B and 41D; towards the base, close to 145C to 145D. Fully opened, upper surface: Close to 48B; towards the base, close to 145C to 145D; with development, color becoming closer to 47D. Fully opened, lower surface: Close to 48C; towards the base, close to 145C to 145D.

*Sepals*.—Quantity and arrangement: Five in a single whorl; proximal 65% of the sepals are fused. Length: About 2 cm. Width: About 1 cm. Shape: Oblong. Apex: Broadly acute. Margin: Entire. Texture, upper and lower surfaces: Smooth, glabrous. Color: When opening, upper surface: Close to 138B. When opening, lower surface: Close to 137B; towards the base, close to 144B and 145A; upper half covered with waxy cuticle, close to 188A. Fully opened, upper surface: Close to 138B. Fully opened, lower surface: Close to 137B; towards the base, close to 138A; upper half covered with waxy cuticle, close to 188A.

*Peduncles*.—Length: About 7 mm to 12 mm. Diameter: About 2 mm to 3 mm. Strength: Strong. Aspect: Erect to about 40° from vertical. Texture: Smooth, glabrous. Color: Close to 136B; waxy cuticle, close to 188A.

*Reproductive organs*.—Stamens: Quantity: About 23, mostly deformed. Anther length: About 5 mm. Anther shape: Irregularly oblong; many partially transformed into petaloids. Anther color: Close to 158D and 159D. Pollen: None observed. Pistils: Quantity: About three per flower. Pistil length: About 2.1 cm. Stigma shape: Pointed; curved. Stigma color: Close to 51B to 51D. Style length: About 1.8 cm. Style color: Close to NN155D. Ovary color: Close to N144C. Fruits and seeds: Fruit and seed development have not been observed on plants of the new Carnation.

Disease & pest resistance: Plants of the new Carnation have not been observed to be resistant to pathogens and pests common to Carnation plants.

Garden performance: Plants of the new Carnation have been observed to have good garden performance and to tolerate wind, rain and temperatures ranging from about 5° C. to about 35° C. and to be hardy to USDA Hardiness Zone 9.

It is claimed:

1. A new and distinct Carnation plant named 'Hilorbli' as illustrated and described.

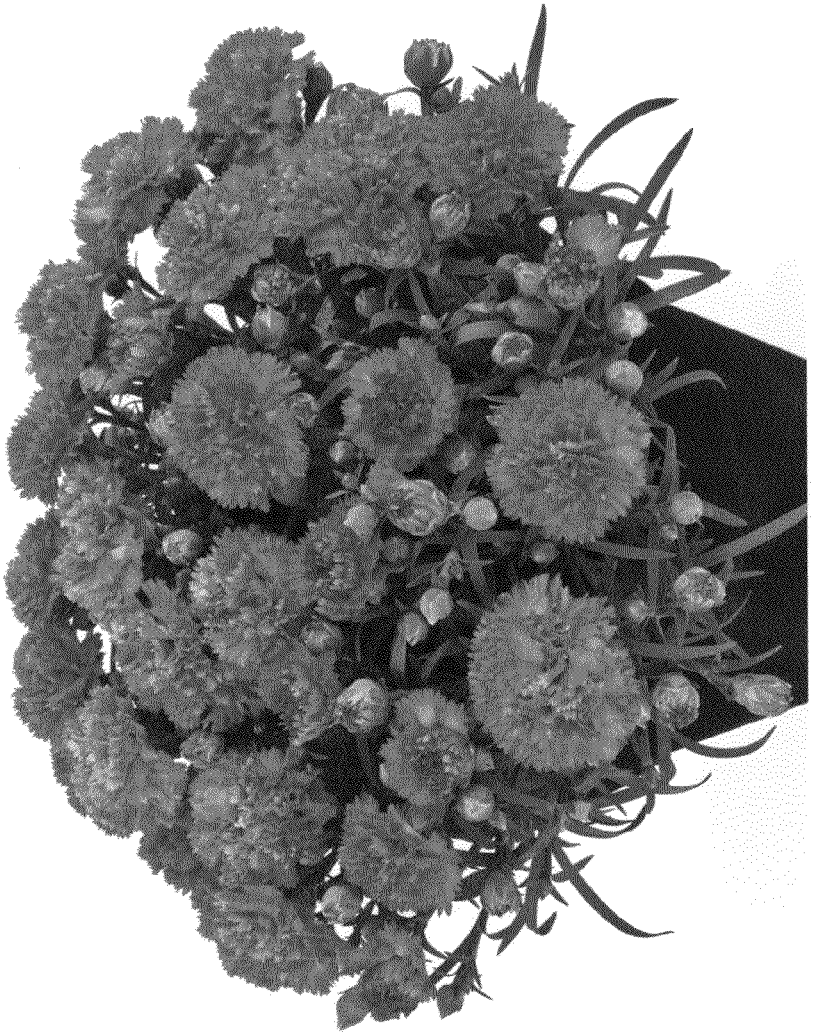

* * * * *